United States Patent [19]

Schaper et al.

[11] 4,362,882
[45] Dec. 7, 1982

[54] 4-METHYL-2,5-DIOXABICYCLO-[4,4,0]-DECAN-3-ONE, ITS PREPARATION AND USE IN PERFUME COMPOSITIONS AND AS AN ODORANT

[75] Inventors: Ulf-Armin Schaper, Düsseldorf; Klaus Bruns, Krefeld-Traar, both of Fed. Rep. of Germany

[73] Assignee: Henkel Kommanditgesellschaft auf Aktien, Dusseldorf-Holthausen, Fed. Rep. of Germany

[21] Appl. No.: 178,082

[22] Filed: Aug. 14, 1980

[30] Foreign Application Priority Data

Sep. 5, 1979 [DE] Fed. Rep. of Germany ....... 2935749

[51] Int. Cl.$^3$ ............................................ C07D 317/06
[52] U.S. Cl. ................................ 549/274; 252/522 R
[58] Field of Search ...................................... 260/340.2

[56] References Cited

U.S. PATENT DOCUMENTS 3,251,857  9/1966  Hostettler et al. ............... 260/340.2
3,952,016  4/1976  Barillo et al. ..................... 260/340.2
4,241,097  12/1980  Sprecker et al. ................ 260/340.2

Primary Examiner—John F. Niebling
Attorney, Agent, or Firm—Hammond & Littell, Weissenberger and Muserlian

[57] ABSTRACT

4-methyl-2,5-dioxabicyclo-[4,4,0]-decan-3-one having the formula

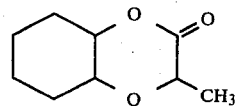

its synthesis, its use as a perfumery agent and as an olefactant component in perfume compositions and as an odorant agent for technical products.

1 Claim, No Drawings

4-METHYL-2,5-DIOXABICYCLO-[4,4,0]-DECAN-3-ONE, ITS PREPARATION AND USE IN PERFUME COMPOSITIONS AND AS AN ODORANT

BACKGROUND OF THE INVENTION

The present invention relates to 4-methyl-2,5-dioxabicyclo-[4,4,0]-decan-3-one in the cis or trans forms or mixtures of the two, which compound is a new fragrance with an interesting scent of castoreum and exceptional staying power.

OBJECTS OF THE INVENTION

An object of the present invention is the obtaining of 4-methyl-2,5-dioxabicyclo-[4,4,0]-decan-3-one.

Another object of the invention is the development of processes for the production of 4-methyl-2,5-dioxabicyclo-[4,4,0]-decan-3-one.

A further object of the present invention is the development of a perfumery composition consisting essentially of from 1% to 50% by weight of at least one enantiomer of 4-methyl-2,5-dioxabicyclo-[4,4,0]-decan-3-one and the remainder customary constituents of perfumery compositions.

A yet further object of the present invention is the development of a method of imparting a pleasant odor to a product comprising adding a sufficient amount of the above perfumery compositions to provide the desired degree of odor.

These and other objects of the invention will become more apparent as the description thereof proceeds.

DESCRIPTION OF THE INVENTION

The above objects have been achieved by the synthesis of the novel compound 4-methyl-2,5-dioxabicyclo-[4,4,0]-decan-3-one having the formula:

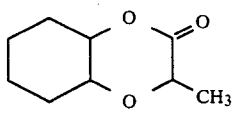

in one or more of its enantiomeric forms. This compound has physical properties and odorant qualities that make it a valuable odorant with an interesting nuance of castoreum and good odor persistency. The new compound according to the invention can be prepared by two methods.

FIRST METHOD

Cyclohexene oxide or 1,2-cyclohexane diol is used as starting material for the first method. These are reacted with lactic acid or α-halopropionic acid or their esters. Generally, a mixture of cis and trans 1,2-cyclohexane diol is reacted with d,l-lactic acid or racemic α-halopropionic acid or their esters in such a manner that a mixture of 4 pairs of enantiomers A to D is produced. This mixture is not separated but used as is as fragrance. The reaction according to this primary synthesis takes place as shown by the following flow diagram:

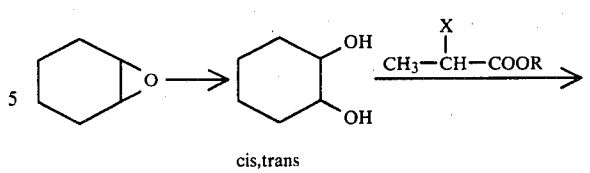

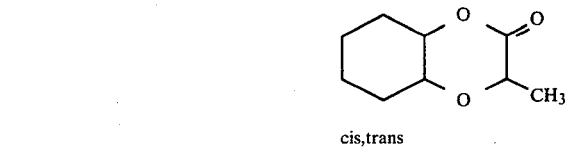

wherein X represents OH, Cl, Br or I and R represents H or lower alkyl. The four enantiomers A to D have the formulas

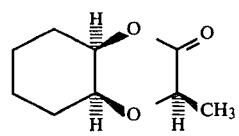

A

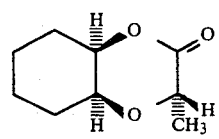

B

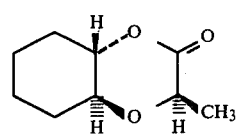

C

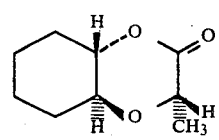

D

In this synthesis, it is most convenient to prepare the ether bond first by reacting the monosodium salt of 1,2-cyclohexane-doil with the ethyl ester of 2-chloropropionic acid at 20° to 200° C. Then, the lactone ring is closed by acid catalysis, according to the flow diagram:

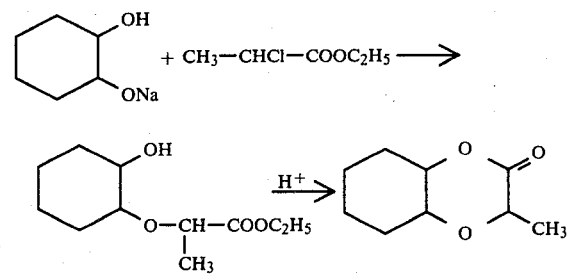

SECOND METHOD

A second synthesis for the compound according to the invention consists of a rearrangement reaction, which occurs during a reacetalization of methylglyoxaldimethylacetal with 1,2-cyclohexane-diol and in the presence of an acid catalyst. The reaction takes place according to the following flow diagram:

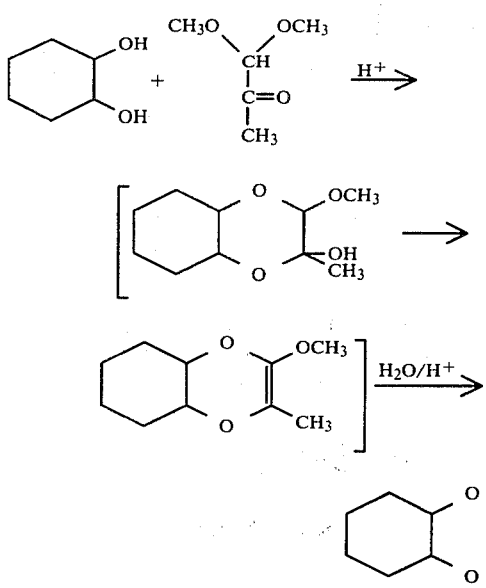

The 4-methyl-2,5-dioxabicyclo-[4,4,0]-decan-3-one obtained by the procedures described above is characterized by an interesting scent of castoreum as well as an exceptional staying power. An additional advantage is its very good ability to combine into novel compositions to which it lends a special staying power as well.

The new fragrance 4-methyl-2,5-dioxabicyclo-[4,4,0]-decan-3-one can be mixed with other fragrances at the most varied ratios to form new perfumery compositions. Its content in the perfumery compositions generally will be from 1% to 50% by weight, related to the total composition.

Such compositions can be used directly as perfumes or for perfuming cosmetic preparations such as cremes, lotions, colognes or toilet waters, aerosols, toilet soaps, etc. The perfumery compositions can also be used for the scenting or reodoring of the various products. For perfuming the various technical products, the compositions generally are added to the former in effective amounts, preferably in concentrations of 0.05% to 2% by weight, related to the total product.

The following examples illustrate the subject matter of the invention in more detail without limiting it, however, to these examples.

EXAMPLE I

Preparation of 4-Methyl-2,5-Dioxabicyclo-[4,4,0]-Decan-3-One (A) By Reaction of 1,2-Cyclohexane Diol with the Ethyl Ester of Chloropropionic Acid 25.3 gm (1.1 mol) of sodium were dissolved in 500 ml of ethanol under dry nitrogen. 116 gm (1 mol) of 1,2-cyclohexane-diol were added to the solution at room temperature. Then, the ethanol was completely removed under vacuum. 163 gm (1.2 mol) of the ethyl ester of 2-chloropropionic acid were added to the mono-sodium salt of 1,2-cyclohexane-diol so obtained, at 50° C., and the mixture was allowed to stand for 5 hours at 80° C. to react further. Then, the reaction mixture was decomposed with water and acidified with sulfuric acid. The organic phase was separated and the aqueous phase was extracted twice with ether. After combining the organic phases, these were washed neutral with water and sodium bicarbonate solution, dried over sodium sulfate and reduced under vacuum. The crude product obtained was distilled under high vacuum. 76 gm of 4-methyl-2,5-dioxabicyclo-[4,4,0]-decan-3-one were obtained with the following analytical data:

| | |
|---|---|
| Bp$_{0.08}$ m bar = 78° to 82° C. | Mp: 57° to 62° C. |
| IR(Oil) | cm$^{-1}$: 2985, 2945, 2870, 1740, 1450, 1370, 1330, 1245, 1235, 1212, 1130, 1065, 885 |
| NMR(CCl$_4$) | δ (ppm): 1.48, d,J = 7 Hz(CH$_3$): 1.2–2.2, m (methylene); 3.4m; 4.1m; 4.5, q,J = 7 Hz (methine). |

The product had a scent of castoreum.

(B) Reacetalization with Methylglyoxal-dimethylacetal 35 gm (0.3 mol) of methylglyoxal-dimethylacetal and 23 gm (0.2 mol) of 1,2-cyclohexane-diol were agitated with 1.5 gm of p-toluenesulfonic acid at 90° to 100° C. for ½ hour. Then, the methanol formed was distilled off under low vacuum over a period of 3 hours, and the excess glyoxal acetal was subsequently removed at 20 m bar. The residue was taken up in ether and washed with sodium carbonate solution until the pH was 8. After drying over sodium sulfate, the solution was reduced by distillation under vacuum. Obtained were 6.5 gm of the product according to the invention with a boiling point at 0.13 m bar of 83° to 86° C. This product was the same as that produced under (A) above.

EXAMPLE 2

| Perfumery Composition After-Shave Base | |
|---|---|
| | Parts by weight |
| 4-methyl-2,5-dioxabicyclo-[4,4,0]-decan-3-one | 50 |
| Boisambrene forte (Henkel) | 200 |
| Bergamot oil | 150 |
| Linalyl acetate | 100 |
| Patchouli oil | 80 |
| Coumarin | 60 |
| Musk ambrette | 50 |
| Oak moss resin | 50 |
| Lavendar oil | 50 |
| Cistus oil (10% DEP) | 50 |
| Vetiveryl acetate | 40 |
| Hydroxycitronellal | 40 |
| Sandal wood oil (H&R) | 40 |
| Cedryl acetate | 30 |
| Vanillin (50% in DEP) | 10 |
| | 1,000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. 4-Methyl-2,5-dioxabicyclo-[4,4,0]-decan-3-one.

* * * * *